Figure 1:
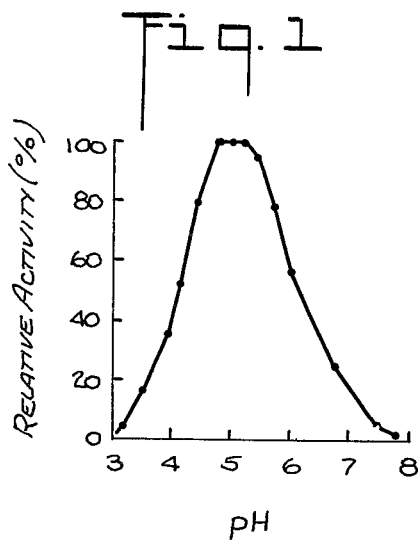

United States Patent [19]

Nakanishi et al.

[11] 4,273,874

[45] Jun. 16, 1981

[54] ACIDIC URICASE AND PROCESS FOR PRODUCTION THEREOF

[75] Inventors: Toru Nakanishi, Atsugi; Yoshimi Shigemasa, Machida, both of Japan

[73] Assignee: Kyowa Hakko Kogyo Co., Ltd., Tokyo, Japan

[21] Appl. No.: 103,579

[22] Filed: Dec. 14, 1979

[30] Foreign Application Priority Data

Dec. 14, 1978 [JP] Japan ................................ 53/153648

[51] Int. Cl.$^3$ ........................... C12N 9/06; C12Q 1/62
[52] U.S. Cl. ...................................... 435/191; 435/10; 435/886
[58] Field of Search ................................... 435/191, 10

[56] References Cited

U.S. PATENT DOCUMENTS

| | | | |
|---|---|---|---|
| 3,431,176 | 3/1969 | Fukumoto et al. | 435/191 |
| 3,475,276 | 10/1969 | Kano | 435/191 |
| 3,616,231 | 10/1971 | Bergmeyer et al. | 435/191 |
| 3,669,843 | 6/1972 | Aunstrup et al. | 435/191 |
| 3,767,533 | 10/1973 | Sugisaki et al. | 435/191 |
| 3,810,820 | 5/1974 | Laboureur et al. | 435/191 |
| 4,062,731 | 12/1977 | Snoke et al. | 435/191 |
| 4,064,010 | 12/1977 | Harris et al. | 435/191 |

*Primary Examiner*—Lionel M. Shapiro
*Attorney, Agent, or Firm*—Fitzpatrick, Cella, Harper & Scinto

[57] ABSTRACT

Acidic uricase is produced by fermentation of a microorganism of the genus Streptomyces. The enzyme is useful for the quantitative determination of uric acid in a sample.

5 Claims, 4 Drawing Figures

ACIDIC URICASE AND PROCESS FOR PRODUCTION THEREOF

BACKGROUND OF THE INVENTION

The present invention relates to uricase having an optimum pH in the acidic region (hereinafter referred to as acidic uricase), a process for production thereof, a method for the quantitative determination of uric acid in a sample by enzymatic reaction and a test composition suitable therefor.

Uricase is a known enzyme which catalyzes the hydrolysis of uric acid to allantoin, hydrogen peroxide and carbon dioxide. The enzyme is, therefore, useful for the determination of uric acid in blood, urine, and the like.

Known uricases have an optimum pH in the neutral or alkaline region. For example, the optimum pH of uricase produced by culturing an *Alternaria tenuis* strain is 7.0 [Arch. Microbiol., vol. 17. 255 (1952)]. Similarly, it is known that uricase having an optimum pH in the range of 8.5–9.5 may be produced from many microorganisms and the like. For example, uricase is recoverable from rat liver [Biochemistry, vol. 13, 888 (1974)], *Aspergillus flavus* [C.R. Acad. Sci., vol. 264, 2244 (1967)], *Candida utilis* [Agric. Biol. Chem., vol. 35, 813 (1971)], *Arthrobacter pascens* [Biochem. Biophys. Acta, vol. 151, 54 (1968)], *Alcaligenes eutrophus* [Arch. Mikrobiol., vol. 60, 160 (1968)], *Bacillus fastidiosus* [Anal. Biochem., vol. 38, 65 (1970)], *Nocardia alba* [Japanese Patent Publication No. 7749/'76], Streptomyces sp. [Agric. Biol. Chem., vol. 33, 1282 (1969)], and *Enterobacter cloacae* [Japanese Published Unexamined Patent Application No. 11296/1979]. The optimum pH of uricase produced by culturing *Trichosporon cutaneum* is around pH 8.0.

It is known that uricase may be used for the determination of uric acid in a sample. According to the known method, uric acid is oxidized with uricase in the presence of oxygen to form allantoin, hydrogen peroxide and carbon dioxide. The amount of uric acid is then calculated by determining at least one of the products formed or, alternatively, by the amount of oxygen consumed in the enzymatic reaction.

In the prior methods, generally, the determination of uric acid is conducted by the determination of hydrogen peroxide formed by a colorimetric method. In that method, the hydrogen peroxide is reacted with a coloring reagent to form a pigment and the absorbancy of the reaction solution is measured.

In the most simple procedure, the enzymatic reaction and color developing reaction is carried out in one step.

The known method, however, suffers from the disadvantage that when the enzymatic reaction is carried out at neutral or alkaline pH, the color-forming reaction is subject to interference from bilirubin, etc. in the blood. While it is desirable to carry out the enzymatic reaction at an acidic pH since a coloring reagent which forms a pigment having high sensitivity in color development can be used, the known uricases do not have an optimum pH within the acidic region.

SUMMARY OF THE INVENTION

It has now been found that a microorganism belonging to the genus Streptomyces produces an acidic uricase and the enzyme is useful for the determination of uric acid.

When the acidic uricase of the present invention is used in the determination of uric acid in blood serum, the amount of sample to be tested may be reduced and the value of precision of the determination is increased, as compared with the methods using uricase having an alkaline optimum pH.

According to the present invention, an acidic uricase having the optimum pH in the acidic region is obtained by culturing a microorganism belonging to the genus Streptomyces which is capable of producing acidic uricase, in a nutrient medium, accumulating the acidic uricase in the culture liquor and recovering the enzyme therefrom.

DESCRIPTION OF THE INVENTION

Acidic uricase of the present invention has the enzymological properties determined as follows.

The enzyme activity is measured according to 4AA-EMAE method described hereinafter. A unit of enzyme activity is defined as the activity of enzyme which decomposes 1 $\mu$mole of uric acid per minute (37° C., pH 5.0).

(1) Action:

Uric acid is oxidized with acidic uricase to form allantoin, hydrogen peroxide and carbon dioxide. The reaction is illustrated as follows:

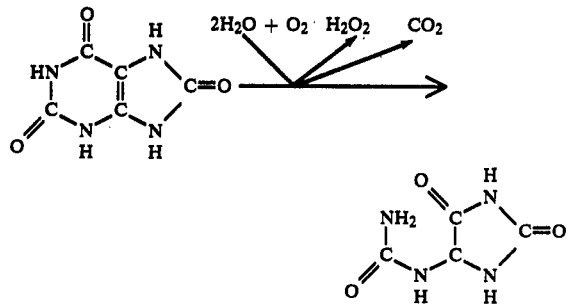

Oxidation of one mole of uric acid liberates one mole of allantoin and generates one mole of hydrogen peroxide and one mole of carbon dioxide.

(2) Optimum pH:

The enzyme preparate is dissolved in various buffers having the pH shown in FIG. 1 to make up enzyme solutions. The amount of enzyme which shows an activity of 20 mu/ml at pH 5.0 is used. As buffers, 1/10 M borate-1/10 M succinate buffer (hereinafter referred to as BS buffer) for pH 3–7 and 1/10 M borate-1/5 M potassium phosphate buffer (hereinafter referred to as BP buffer) for pH 7 or more are used.

The same enzyme activity determination procedures as in the 4AA-EMAE method described hereinafter are repeated except that buffer solutions having the pH shown in FIG. 1 are used instead of the buffer solution in the 4AA-EMAE method. FIG. 1 shows the relative activity at each pH, activity at pH 5.0 being defined as 100. The optimum pH is found to be 4.7–5.1.

Figure 2:
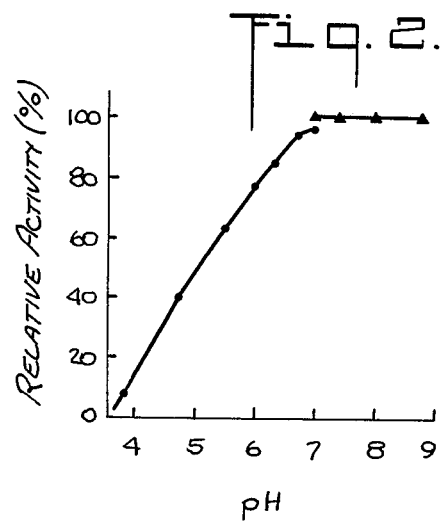

(3) pH stability:

The enzyme preparate is dissolved in various buffer solutions having the pH indicated in FIG. 2 to make up enzyme solutions having an activity of 0.4 u/ml. As buffer solutions, BP buffer for pH 7.0–9.0 and BS buffer for pH 3.0–7.0 are used.

Each enzyme solution is incubated at 29° C. for 16 hours. Then the solutions are diluted by 20 times and adjusted to a pH of 5.0. The activities of the enzyme solutions are determined according to the 4AA-EMAE method; and FIG. 2 shows the relative activity on each pH, the highest activity being defined as 100.

The present enzyme is stable at a pH of 7.0 or more.

Figure 3:
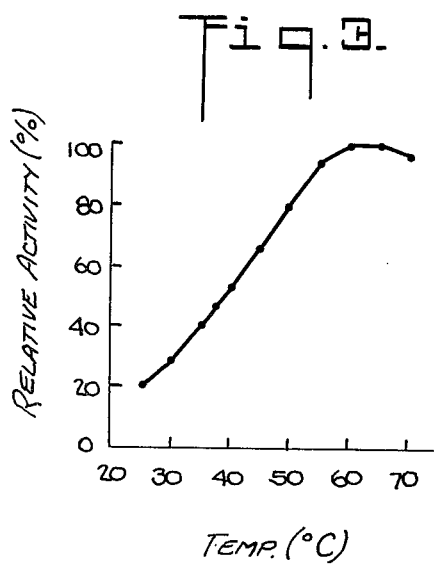

(4) Optimum temperature:

The enzyme preparate is dissolved in BS buffer (pH 5.0) to make up an enzyme solution having an activity of 0.02 u/ml. The same enzyme activity determination procedures as in the 4AA-EMAE method described hereinafter are repeated except that the enzyme reaction is carried out at the temperature indicated in FIG. 3. FIG. 3 shows the enzyme activity at each temperature, the highest activity being defined as 100. The optimum temperature of the present enzyme is found to be 60°–65° C.

Figure 4:
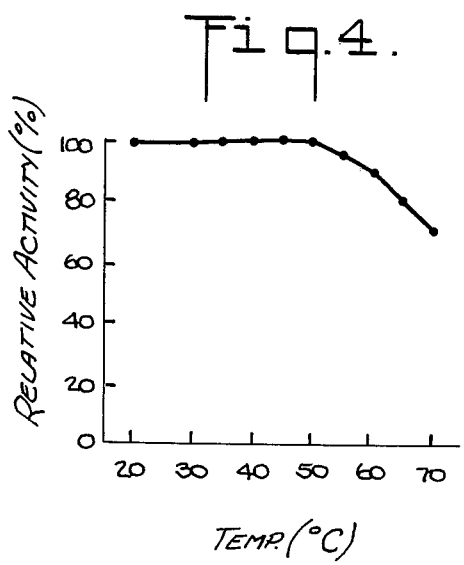

(5) Heat stability:

The enzyme preparate is dissolved in BS-buffer solution (pH 5.0) to make up an enzyme solution having an activity of 0.02 u/ml. The enzyme solutions are incubated for 30 minutes at the temperatures indicated in FIG. 4 and then the enzyme activity is determined at a temperature of 37° C. according to the 4AA-EMAE method. FIG. 4 shows the relative activity on each temperature, the highest activity being defined as 100. The activity of the present enzyme is not lost by the treatment at a temperature of 50° C. for 30 minutes and about 90% enzyme activity remains after treatment at a temperature of 60° C. for 30 minutes.

(6) Substrate specificity:

The enzyme preparate is dissolved in BS-buffer (pH 5.0) to make up an enzyme solution having an activity of 0.02 u/ml. The same enzyme activity determination procedures as in the 4AA-EMAE method described hereinafter are repeated except that the substrates shown in Table 1 are used. The relative activity on several substrates is as follows:

TABLE 1

| Substrate | Relative activity |
| --- | --- |
| Uric acid | 100 |
| Adenine | 0 |
| Guanine | 0 |
| Xanthine | 0 |
| Hypoxanthine | 0 |
| Theobromine | 0 |
| Theophylline | 0 |

The 4AA-EMAE method referred to above is carried out as follows.

(1) Reagent (1-1) Buffer solution: BS buffer [1/10 M borate-1/10 M succinate buffer (pH 5.0)]

(1-2) EDTA solution: 28 mg of disodium ethylenediaminetetra acetate.dihydrate dissolved in 100 ml of water.

(1-3) Coloring solution: 40 mg of 4-amino-antipyrine, 10 mg of N-ethyl-N-(3-methylphenyl)-N'-acetylethylenediamine (hereinafter referred to as EMAE) and 500 U of peroxidase (Purpurogallin unit) dissolved in 100 ml of water.

(1-4) Uric acid solution: 20 mg of uric acid dissolved in 100 ml of water.

(2) Determination procedure

In this procedure 0.65 ml of BS-buffer solution, 0.2 ml of EDTA-solution and 0.65 ml of coloring solution are added to 0.5 ml of enzyme solution of which the uricase activity is to be determined. The mixture is then incubated at 37° C. for about 5 minutes and 1 ml of uric acid solution is added to the mixture. The mixture is incubated at 37° C. for 5 minutes. After ice cooling the absorbancy of the reaction solution is measured at 550 nm.

As a comparison, the same procedure is repeated except that 1 ml of deionized water is used instead of the uric acid solution. The amount of hydrogen peroxide generated is calculated from the difference in absorbancy; and the amount of uric acid is calculated from the amount of hydrogen peroxide generated.

Acidic uricase of the present invention is produced by culturing a microorganism belonging to the genus Streptomyces. Any microorganism belonging to the genus Streptomyces and capable of producing acidic uricase may be used. A preferred species is *Streptomyces gannmycicus* and an example of a preferred strain is *Streptomyces gannmycicus* ATCC 27434, the microbiological properties of which are disclosed in Intern. J. Syst. Bacteriol. vol. 22, 300 (1972).

Either a synthetic or natural medium may be used for culturing of the microorganism as long as it contains an appropriate carbon source, nitrogen source, inorganic materials and other nutrients which are assimilable by the particular strain utilized.

As a carbon source, various carbohydrates such as glucose, fructose, sucrose, dextrin, molasses, starch, etc., alcohols such as glycerol, sorbitol, manitol, etc., organic acids such as uric acid, acetic acid, pyruvic acid, etc., amino acids, hydrocarbons and the like may be used.

As nitrogen sources, ammonia, inorganic and organic ammonium salts such as ammonium chloride, ammonium carbonate, ammonium phosphate, ammonium sulfate, ammonium nitrate, ammonium acetate etc., urea, amino acids such as glutamic acid, uric acid and other nitrogen-containing compounds as well as nitrogenous organic materials such as peptone, NZ-amine, meat extract, yeast extract, corn steep liquor, soybean powder, defatted soybean, dry yeast, casamino acid, soluble vegetable protein and the like may be used.

As inorganic materials, potassium dihydrogen phosphate, dipotassium hydrogen phosphate, magnesium sulfate, ferrous sulfate, manganese sulfate, zinc sulfate, sodium chloride, potassium chloride, calcium carbonate, etc. may be used.

Although acidic uricase can be produced when using a medium without an enzyme inducer such as uric acid, the yield of acidic uricase can be enhanced by adding uric acid or a uric acid-containing natural substance to the medium as an enzyme inducer.

Culturing is generally carried out at a temperature of 22°–40° C., preferably 25°–35° C. and at around neutral pH. Culturing is continued until the enzyme is formed and detected in the culture liquor, generally for 1–3 days. Under these conditions, a considerable amount of the enzyme is formed in the culture liquor and/or within the microbial cells.

After completion of the culturing, the microbial cells are disrupted by appropriate means such as ultrasonic disintegration, grinding, etc. to obtain a cell extract and the extract is subjected to centrifugation to obtain a supernatant. Then the supernatant is subjected to conventional purification methods such as salting-out, dialysis, chromatography using ion exchange cellulose, Sephadex, and the like to obtain the purified enzyme.

Basically, the method and test composition according to the present invention for the determination of uric acid in a sample comprises a system for oxidizing uric acid with acidic uricase and a system for determining the amount of at least one of the products formed in the acidic uricase reaction or the amount of oxygen consumed in the enzymatic reaction.

According to the present invention, the determination of uric acid may be performed by conducting the individual systems stepwise and may preferably be performed by subjecting the sample to enzymatic reaction and a color-forming reaction with a reagent comprising acidic uricase and a detecting system for at least one of the products formed by the enzymatic reaction. An example of a preferred detecting system is a hydrogen peroxide detecting system which comprises peroxidase and a coloring reagent.

Several methods for the determination of hydrogen peroxide are known. Representative methods include:

(1) reacting hydrogen peroxide with a coloring reagent in the presence of peroxidase to form a pigment and determining the pigment colorimetrically;

(2) reacting hydrogen peroxide with alcohol in the presence of catalase to form an aldehyde, reacting the aldehyde with acetyl acetone and ammonia to form a pigment and determining the pigment colorimetrically; and (3) reacting hydrogen peroxide with alcohol in the presence of catalase to form an aldehyde, reacting the aldehyde with the reduced form of nicotineamide adenine dinucleotide (hereinafter referred to as NADH) to form nicotineamide adenine dinucloeotide (hereinafter referred to as NAD) and determining NAD colorimetrically.

Among these methods, the method using peroxidase is very simple and the determination of hydrogen peroxide is performed by measuring the absorbancy of the reaction solution based on the color development of formed pigment with a spectrophotometer.

The color development of a pigment may be expressed by molecular extinction coefficient. That is, if the molecular extinction coefficient is large, the sensitivity of color development is good. The amount of sample to be tested can be reduced as the sensitivity of color development becomes better. Molecular extinction coefficients ($\times 10^4$) of a pigment formed by reacting hydrogen peroxide with various coloring reagents in the presence of peroxidase are determined and shown in Table 2.

TABLE 2

| | Coloring reagent | | | |
|---|---|---|---|---|
| | 4AA phenol | 4AA-DMA | 4AA-EMAE | MBTH-DMA |
| | Measured wavelength | | | |
| pH | 500 nm | 550 nm | 550 nm | 550 nm |
| 3.0 | —*1 | —*1 | —*1 | 8.22 |
| 4.0 | —*1 | 1.86 | 2.76 | 7.54 |
| 5.0 | 0.16 | 2.00 | 3.06 | 5.89 |
| 7.0 | 1.07 | 1.62 | 3.60 | —*2 |
| 8.0 | 1.15 | 1.36 | 3.43 | —*2 |
| 9.0 | 0.94 | 0.98 | 2.98 | —*2 |

Note:
1 The absorbancy is measured at the maximum absorbancy wavelength of the pigment.
2 4AA: 4-Aminoantipyrine
DMA: N,N-Dimethylaniline
EMAE: N-Ethyl-N-meta-methylphenyl-N'-acetylethylenediamine
MBTH: 3-Methyl-2-benzothiazoline-hydrazone-HCl
*1: Reaction does not proceed and therefore no pigment is formed.
*2: Reaction proceeds in the absence of H$_2$O$_2$ and therefore the determination is meaningless.

Example of the coloring reagents are 4AA-phenol, 4AA-DMA, 4AA-EMAE, MBTH-DMA, MBTH-phenol, 4AA-DEA (DEA: Diethylaniline), 4AA-DBA (DBA: Dibutylaniline), MBTH-DEA, MBTH-DBA, Leucocrystals violet, MBTH-SS acid and the like.

As it is apparent from the above Table 2, the pigment formed using 4AA-phenol shows a stable color development in the neutral to weak alkaline region but the extinction coefficient is small. On the other hand, the pigment formed using 4AA-DMA shows a stable color development in the acidic to neutral region and the extinction coefficient is higher than that of 4AA-phenol. The pigment formed using 4AA-EMAE shows a stable color development in a wide range of the acidic to alkaline region and the extinction coefficient is higher than that of 4AA-DMA. The pigment formed using MBTH-DMA shows a relatively stable color development in the acidic region and the extinction coefficient is the highest of the four coloring reagents. Since it is advantageous to use a coloring reagent which is stable in the acidic region and has a high sensitivity in development of color, preferred coloring reagents include MBTH-DMA, 4AA-EMAE and 4AA-DMA. The coloring reagent is used in a concentration of 0.2–20 mmol/l.

When the sample is an oily substance, a surfactant such as polyethyleneglycol, polyethyleneglycolalkylphenyl ether, and the like, is added to the sample to improve the affinity with the reagent solution. The surfactant is used in a concentration of 0.01–5 g/l.

As a stabilizing reagent, disodium salt of ethylenediamine tetra-acetic acid (hereinafter referred to as EDTA) and the like are used.

As a buffer solution, borate buffer, phosphate buffer, tris-hydrochloride buffer, tris-maleate-hydrooxide buffer, citrate-disodium phosphate buffer, succinate-borate buffer, phosphate-borate buffer and the like are used in a concentration of 0.005–0.5 mol/l.

The enzymatic reaction is carried out at a temperature of 20°–75° C., preferably 35°–70° C., and at a pH of 3–6 preferably at a pH of 4–5, for 1–30 minutes.

After the enzymatic reaction, the absorbancy of the reaction solution is measured at a visible ray region.

The enzyme reagent comprising acidic uricase, peroxidase, and coloring reagent is a useful test composition for the determination of uric acid. The composition may be used in various forms. For example, the ingredients may be mixed in liquid form or powder form. The powdered formulation may be readily reconstituted for later use simply by the addition of buffer solution.

Certain specific embodiments of the invention are illustrated by the following representative examples.

EXAMPLE 1

In this example, *Streptomyces gannmycicus* ATCC 27434 is used as a seed strain. One loopful of the seed strain is inoculated into 300 ml of a seed medium comprising 2 g/dl glucose, 1 g/dl meat extract, 0.5 g/dl corn steep liquor, 0.5 g/dl peptone, 0.1 g/dl yeast extract, 0.1 g/dl KH$_2$PO$_4$, 0.05 g/dl MgSO$_4$.7H$_2$O and 0.1 mg/dl FeSO$_4$.7H$_2$O (pH 7.2 before sterilization) in a 2 l-Erlenmeyer flask. Culturing is carried out with shaking at 30° C. for 42 hours.

All of the resulting seed culture is inoculated into 18 l of the same medium as the seed medium in a 30 l-jar fermenter. Main fermentation is carried out with aeration of 0.5 l/l (medium)/min. and stirring at 250 r.p.m. for 30 hours at 30° C.

After the completion of culturing, the culture liquor is centrifuged, whereby 950 g (wet weight) of microbial cells is obtained. The cells are mixed with 10 l of 0.05 M borate buffer (pH 7.8) and subjected to centrifugation again. The thus obtained cells are suspended in 5 l of 0.05 M borate buffer (M/80 borax-M/20 borate buffer) (pH 7.8) and then disrupted in a Dyno Laboratory Mill KDL type (made by Willy A. Bachofen Inc., Switzerland). The resulting disrupted cell suspension is centrifuged to obtain a supernatant which exhibits uricase activity of 6.25 u/dl (volume of the supernatant: 4.5 l, total activity: 281.25 u).

To the supernatant, ammonium sulfate is added to 30% saturation, and the precipitate is removed by centrifugation. The thus obtained supernatant is further mixed with ammonium sulfate to 60% saturation. The formed precipitate is recovered by centrifugation and dissolved in 1.0 l of 0.05 M borate buffer (pH 7.8). The resulting solution is dialyzed against 50 l of the same borate buffer using a cellophane tube as a dialysis membrane at 5° C. overnight. Then, acetone is added to the solution in the dialysis tube to make 30% (V/V) acetone solution, and the formed precipitate is removed by centrifugation. Then, acetone is added to the supernatant to make 60% (V/V) acetone solution. The precipitate is recovered by centrifugation and dissolved in 360 ml of 0.05 M borate buffer (pH 7.8). The resulting solution is dialyzed against 50 l of the same borate buffer using a cellophane tube as a dialysis membrane at 5° C. overnight. Then, the solution in the dialysis tube is heated at 60° C. for 30 minutes, whereby catalase is inactivated. The heat treated solution is passed through a column of DEAE-Sephadex A 50 (weakly basic Sephadex ion-exchange material, Sephadex: trade name for molecular sieve of dextran derivative made by Pharmacia Fine Chemicals Inc., U.S.A.) (1000 ml) equilibrated in advance with 0.2 M NaCl. After the column is washed with 1 l of 0.05 M borate buffer (pH 7.8), concentration gradient elution is carried out with 1 l of the same borate buffer containing 0.2 M NaCl and 1 l of the same borate buffer containing 0.7 M NaCl. The eluate is taken in 20 g fractions, and the active fractions of uricase are combined and mixed with ammonium sulfate to 60% saturation. The formed precipitate is recovered by centrifugation and is dissolved in 90 ml of 0.05 M borate buffer (pH 7.8). Then, the resulting solution is charged on a column of Sephadex G 200 (4.2×98.5 cm) equilibrated in advance with 0.05 M borate buffer (pH 7.8), and elution is carried out with the same buffer. The active fractions of uricase are combined and mixed with ammonium sulfate to 60% saturation. The formed precipitate is recovered by centrifugation and dissolved in 35 ml of 0.05 M borate buffer (pH 7.8). The resulting enzyme solution is again passed through a column of Sephadex G 200 (2.8×69.5 cm) equilibrated in advance with 0.05 M borate buffer (pH 7.8), and elution is carried out with the same buffer. Then, the active fractions are combined and mixed with ammonium sulfate to 60% saturation. The formed precipitate is recovered by centrifugation and dissolved in 25 ml of 0.05 M borate buffer (pH 7.8). The resulting solution is dialyzed against about 20 l of 0.05 M borate buffer (pH 7.8) using a cellophane tube as a dialysis membrane at 5° C. overnight. Thereafter, the solution in the dialysis tube is charged on a column of 200 ml of DEAE-cellulose equilibrated in advance with 0.05 M borate buffer (pH 7.8). After the column is washed with 200 ml of 0.05 M borate buffer (pH 7.8), concentration gradient elution is carried out with 500 ml of the same buffer and 500 ml of 0.05 M borate buffer (pH 7.8) containing 0.7 M NaCl. The eluate is taken in 10 g fractions, and the active fractions of uricase are combined and mixed with ammonium sulfate to 60% saturation. The formed precipitate is recovered by centrifugation and then dissolved in about 20 ml of 0.05 M borate buffer (pH 7.8). The resulting solution is dialyzed against 10 l of the same borate buffer using a cellophane tube as a dialysis membrane at 5° C. overnight. Thereafter, the solution in the dialysis tube is freeze-dried, whereby a powder of acidic uricase is obtained (specific activity: 3.74 u/mg protein). The yield in terms of activity based on the supernatant obtained by centrifuging the disrupted cell suspension is 20.3%.

The properties of the obtained enzyme preparate are as described above.

EXAMPLE 2

In this example, the quantitative determination of uric acid using MBTH-DMA is conducted.

(A) Reagent (a) buffer: M/10 borax-M/10 succinate buffer (pH 4.0 or pH 5.0)
(b) 1.5 mg/ml EDTA.disodium.dihydrate
(c) 5% (W/V) Triton X-100 (trade name for a surface-active agent; polyethyleneglycol alkylphenyl ether; Rohm & Haas Co.)
(d) 1.5 mg/ml MBTH
(e) 1.0 mg/ml DMA
(f) 200 u (Purpurogallin unit)/ml peroxidase
(g) 2.0 u/ml acidic uricase [0.05 M borate buffer (pH 7.5)]
(h) pure water
(i) aqueous solution of uric acid (2, 5 or 10 mg/dl)

(B) Procedures 2.40 ml of (a) (pH 4.0 or 5.0), 0.05 ml of (b), 0.05 ml of (c), 0.10 ml of (d), 0.10 ml of (e), 0.10 ml of (f), 0.10 ml of (g), and 0.05 ml or 0.08 ml of (h) are mixed and preliminarily heated at 37° C. for 5 minutes. To the mixture there is added 0.05 ml or 0.02 ml of (i) (to make a total volume of 3.0 ml) and the mixture is allowed to react at 37° C. for 5 minutes. Thereafter, the absorbancy at 550 nm is measured by a spectrophotometer. As a control, the same procedures are repeated except that pure water is used instead of (i) and the absorbancy at 550 nm is measured.

Based on the difference in absorbancy between the test solution and control solution, the amount of formed $H_2O_2$ is calculated, and the amount of uric acid is calculated based on the amount of $H_2O_2$. The results are shown in Table 3.

As obvious from Table 3, the present method for the quantitative determination of uric acid is a very effective one by which a slight amount of uric acid, i.e. 0.4 μg to 5.0 μg in the sample can be determined with great precision in a one step reaction.

TABLE 3

| pH of reaction mixture | Concentration of uric acid solution (mg/dl) | Amount of uric acid solution added (μl) | Amount of uric acid added (μg) | Absorbancy at 550 nm | Amount of $H_2O_2$ formed (mμ moles/ reaction system) | Amount of uric acid determined (μg) | Recovery of uric acid (%) |
|---|---|---|---|---|---|---|---|
| 5.0 | 2 | 20 | 0.4 | 0.022 | 2.241 | 0.376 | 94.0 |

TABLE 3-continued

| pH of reaction mixture | Concentration of uric acid solution (mg/dl) | Amount of uric acid solution added (μl) | Amount of uric acid added (μg) | Absorbancy at 550 nm | Amount of H$_2$O$_2$ formed (mμ moles/ reaction system) | Amount of uric acid determined (μg) | Recovery of uric acid (%) |
|---|---|---|---|---|---|---|---|
| | 5 | 20 | 1.0 | 0.059 | 6.010 | 1.010 | 101.0 |
| | 10 | 20 | 2.0 | 0.116 | 11.817 | 1.987 | 99.4 |
| | 2 | 50 | 1.0 | 0.057 | 5.806 | 0.976 | 97.6 |
| | 5 | 50 | 2.5 | 0.145 | 14.771 | 2.483 | 99.3 |
| | 10 | 50 | 5.0 | 0.294 | 29.949 | 5.035 | 100.7 |
| 4.0 | 2 | 20 | 0.4 | 0.031 | 2.467 | 0.415 | 103.7 |
| | 5 | 20 | 1.0 | 0.076 | 6.048 | 1.017 | 101.7 |
| | 10 | 20 | 2.0 | 0.149 | 11.857 | 1.993 | 99.7 |
| | 2 | 50 | 1.0 | 0.077 | 6.127 | 1.030 | 103.0 |
| | 5 | 50 | 2.5 | 0.188 | 14.960 | 2.514 | 100.7 |
| | 10 | 50 | 5.0 | 0.375 | 29.841 | 5.017 | 100.3 |

What is claimed is:

1. Acidic uricase having an optimum pH in the range of 4.7 to 5.1, and characterized by catalyzing the oxidation of uric acid to allantoin.

2. A process for producing acidic uricase which comprises culturing a microorganism belonging to the genus Streptomyces which is capable of producing acidic uricase having an optimum pH in the range of 4.7 to 5.1, and characterized by catalyzing the oxidation of uric acid to allantoin in a nutrient medium until enzymatic activity is detected in the culture liquor and thereafter recovering said acidic uricase therefrom.

3. A process according to claim 2 wherein said microorganism belongs to the species *Streptomyces gannmycicus*.

4. A process according to claim 3 wherein said microorganism has the identifying characteristics of *Streptomyces gannmycicus* ATCC 27434.

5. A process according to claim 2 wherein said culturing is carried out at 25° to 35° C. for 1 to 3 days at about neutral pH.

* * * * *